United States Patent [19]

Palomo-Coll et al.

[11] 4,405,782

[45] Sep. 20, 1983

[54] PROCESS FOR THE PREPARATION OF SOLUTIONS OF 7-AMINOCEPHALOSPORANIC ACIDS

[75] Inventors: Alberto Palomo-Coll; Antonio L. Palomo-Coll, both of Barcelona, Spain

[73] Assignee: GEMA, S.A., Spain

[21] Appl. No.: 323,403

[22] Filed: Nov. 20, 1981

[30] Foreign Application Priority Data

Nov. 22, 1980 [ES] Spain .................................. 497.076
Jul. 16, 1981 [ES] Spain .................................. 504.011

[51] Int. Cl.³ .................. C07D 501/18; A61K 31/545
[52] U.S. Cl. ...................................... 544/21; 544/16; 544/23; 424/246
[58] Field of Search .................. 544/21, 23, 22, 16, 544/26, 27; 424/246

[56] References Cited

U.S. PATENT DOCUMENTS 3,965,098 6/1976 Robinson .............................. 544/23
4,051,131 9/1977 Robinson .............................. 544/23

Primary Examiner—Nicholas S. Rizzo
Attorney, Agent, or Firm—Scully, Scott, Murphy & Presser

[57] ABSTRACT

A process for the preparation of solutions of 7-aminocephalosporanic acids wherein there is obtained a salt of the general formula III:

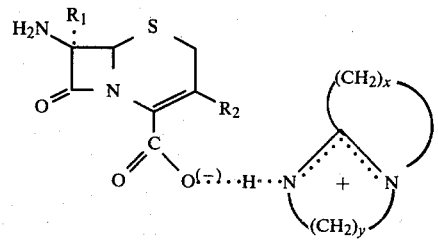

where $R_1$ may be a group selected from among hydrogen, methyl, or a low molecular weight alkoxy, $R_2$ is a group selected from among methyl, methoxy, azido, chlorine, carbamoylmethyl, acetoxy, thiomethyl, phenylthiomethyl and others, x means from 3 to 5 carbon atoms and y means from 2 to 4 carbon atoms is disclosed. The process is based on the reaction of a compound of formula I

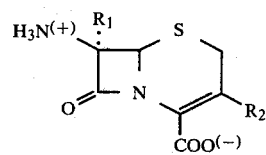

with a bicyclic amidine.

7 Claims, No Drawings

PROCESS FOR THE PREPARATION OF SOLUTIONS OF 7-AMINOCEPHALOSPORANIC ACIDS

FIELD OF THE INVENTION

The present invention relates to a process for the preparation of solutions of 7-aminocephalosporanic acids, of interest in the manufacture of cephalosporins, antibiotics of use in human and veterinary medicine.

DESCRIPTION OF THE PRIOR ART

The methods known and used in industrial practice for the preparation of solutions of 7-aminocephalosporanic acids consist of reacting one of said acids with a tertiary amine, preferably triethylamine, in an aqueous medium, water-acetone or in methylene chloride.

The use of water-organic solvent miscible systems has the following drawbacks:

1. Partial hydrolysis of the acylation reagent, acid chloride, anhydride or mixed anhydride.
2. Difficulties in the isolation of the antibiotic, the use of more or less complex extraction methods being required.
3. The more laborious purification, to separate the contaminating starting products.
4. Certain cephalosporins, as acids, produce gels on precipitating in an aqueous medium and others are sufficiently soluble in water and require large amounts of organic solvent for their isolation.

Attempts were made to solve these problems by techniques making the use of organic solvents possible.

The most usual of such solvents, dichloromethane has become widely used in industry with 7-aminocephalosporanic acid. Nevertheless, with this product at least two equivalents of triethylamine per equivalent of acid are required to obtain solution. The amount of this tertiary amine required is much higher when 1,2-dichloroethane is used.

The limitation of the organic solvent, on the one hand and the excess of base, on the other, was overcome by the silylation techniques introduced by Stolberg (Grünenthal, 1,159,449) in the case of 6-aminopenicillanic acid and its use was extended to the 7-aminocephalosporanic acids. This practice is well known to the experts in the art and the number of patents in this field is too numerous to list herein.

It is also known that 7-amino-desacetoxycephalosporanic acid does not form solutions in dichloromethane with tertiary amines, namely triethylamine, the most effective base for this purpose. Its solutions are compromised, therefore, by the use of two equivalents of the amine and two equivalents of trimethylchlorosilane. Generally speaking, when working with the group of 7-aminocephalosporanic acids, two equivalents of silylating agent are required to form the N,O-bis trimethylsilyl derivative, to obtain the desired solution.

A very peculiar characteristic property of the compounds integrating the group of 7-aminocephalosporanic acids, associated with their purity, is the impossibility of forming solutions with triethylamine in dichloromethane, dimethylformamide, dimethylacetamide and acetonitrile, among other solvents.

Thus, for example, when very impure 7-amino-3-(5-methyl-1,3,4-thiadiazol-2-yl-thiomethyl)-3-cephem-4-carboxylic acid is used, deteriorated solutions are obtained with triethylamine; at least two equivalents are required in dimethylformamide, acetonitrile and partly in methylene chloride. Nevertheless, it has been impossible to form such solutions with pure product. The same also happens with similar derivatives, as described in the literature (DeMarinis et al.; J. Med. Chem., 19, 754; 1976).

It is obvious that the use of such 7-aminocephalosporanic acids in the acylation reactions causes very complex problems for the preparation of the pure antibiotic and the yields are generally low.

Another peculiar fact added to the above difficulties is the impossibility of the acylation reaction between the mixed anhydrides of amino acid enamine salts and pivaloyl chloride with the silylated derivatives, a technique which is restricted to the use of 6-aminopenicillanic acid. German Pat. No. 22.63.861 discloses the difficulties of forming triethylamine salts of those acids and their acylation, proposing methanol as appropriate solvent for preparing solutions as triethylamine salts. Although the yields are excellent, the cephalosporin isolation technique is complicated by the need to evaporate the methanol at reduced pressure. In the said patent, there is also disclosed the preparation of a methanol solution of the triethylamine salt of 7-amino-3-(5-methyl-1,3,4-thiadiazol-2-yl-thiomethyl)3-cephem-4-carboxylic acid. Example 1 of Swiss Pat. No. 535.261 also discards the preparation of the triethylamine salt of this acid in dichloromethane and in Example 2 the solution corresponding to 7-amino-3-(1-methyl-tetrazol-5-yl)-3-cephem-4-carboxylic acid. This compound and its triethylamine salt solution, also described in the scientific literature (Nannini et al., Arzneim-Forsch./Drug. Res. 27 (1) 2,352 (1977) and for similar heterocycles (DeMarinis et al., J. Med. Chem., 19, 754 (1976).

Several examples of German Pat. No. 27.58.000 describe the use of a solution of 7-aminocephalosporanic acid in dichloromethane, in the triethylamine salt form. About three equivalents of triethylamine per equivalent of 7-aminocephalosporanic acid are used in Example 1 (2) and Example 6 is similar for 7-amino-3-(2-amino-1,3,4-thiadiazol-5-yl-thiomethyl)-3-cephem-4-carboxylic acid. German Laid Open Patent application No. 21.63.514 discloses the difficulties and complications in the acylation reaction of triethylamine salts, for which reason the use of reactants for the silylation of 7-aminocephalosporanic acids is preferred. A chlorosilane derivative and the corresponding equivalents of a tertiary amine are used. The reactant in general should be used in conformity with the water content in the solvents and products. In U.S. Pat. No. 3,741,965 there are used three equivalents of trimethylchlorosilane and tertiary base per equivalent of 7-amino-3-(3-methylisoxazol-5-yl)carbonylthiomethyl-3-cephem-4-carboxylic acid. These silylation reactions are usually effected by heating of the mixture and particularly with 3-thionyl substituted 7-aminocephalosporanic acids. With these pure compounds, the silylation requires extended heating times, for subsequent cooling to the reaction temperature.

The following results have been determined for the solubility of one centimole of 3-substituted 7-amino-3-cephem-4-carboxylic acid in 15 and 20 ml of organic solvent:

3-acetoxymethyl. It is not possible to form a solution in dichloromethane, 1,2-dichloroethane, acetonitrile, dimethylformamide, dimethylacetamide, chloroform, isopropanol and methanol with one equivalent of triethylamine. No solution is formed in 1,2-dichloroethane, chloroform, dimethylacetamide and isopropanol with two equivalents of triethylamine. Solutions are formed in nitromethane and methanol.

3-azidomethyl. No solutions were formed with one equivalent of triethylamine in any of the above solvents. With two equivalents, solutions were obtained only in dimethylformamide, nitromethane, acetonitrile and methanol.

3-methyl. Insoluble with over three equivalents of triethylamine in all the foregoing solvents, except methanol.

3-thiomethyl derivatives. No solution was obtained with the tertiary base in any of the solvents recited herein.

3-heterocyclo-2-yl derivatives. These include the 7-amino-3(1,3,4-thiadiazol-2-yl)-3-cephem-4-carboxylic acids and the derivatives having a 1,3,4-thiazole, 1,3,4-oxadiazole ring in place of the thiadiazole as substituents. No triethylamine solutions were obtained. No solutions were obtained either with compounds having heterocycles condensed to 7-member rings.

Other usual tertiary amines were completely ineffective.

The above results have been obtained with technically pure compounds. In certain cases the low purity products gave solutions or pseudosolutions which then produce, in the acylation reaction, a low yield and require subsequent complex treatments for purification of the cephalosporin, as disclosed in certain patents; for example in those mentioned hereinbefore, and in scientific publications.

SUMMARY OF THE INVENTION

According to the present invention, the preparation of solutions of a compound from the group comprising the 7-aminocephalosporanic acids is effected with a compound of the following general formula:

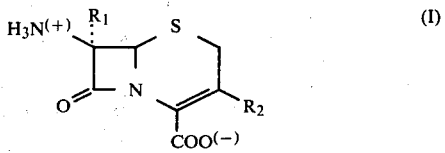

wherein $R_1$ may be H or a low molecular weight group such as methoxy or methyl and $R_2$ a group selected from among hydrogen, methyl, acetoxymethyl, methoxy, chlorine, carbamoyloxymethyl, azido or a thiomethyl, phenylthiomethyl, aliphatic methylthiocarbonyl having from two to four carbon atoms, aromatic methylthiocarbonyl, methylthiocarbonyl heterocyclo derivative having a five or six member ring with at least one atom of oxygen, sulphur or nitrogen, methylthioheterocyclo derivatives of thiazole, thiadiazole, triazole or tetrazole, pyridine, pyrimidine or heterocycles condensed to an aromatic ring, or a thiadizolyl radical, oxadiazolyl or triazolyl; which is reacted with a bicyclic amidine having the following general formula:

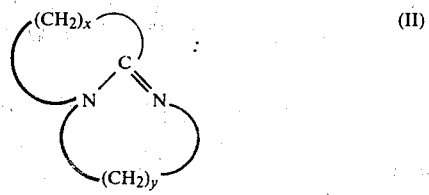

wherein X means from 3 to 5 carbon atoms and Y from 2 to 4 to obtain a salt having the following general formula:

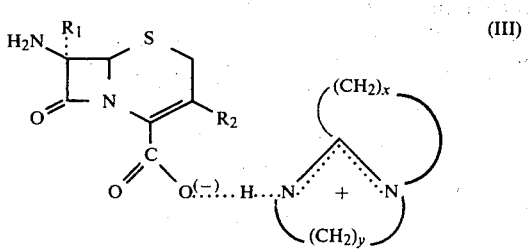

The product resulting from the above combination gives soluble salts in different organic solvents.

The bicyclic amidines of Formula II are known compounds, the properties and use of which in synthesis have been described by Oediger, Möller and Eiter (Synthesis, 591; 1972). Among these, 1,5-diazabicyclo (4,3,0) non-5-ene (DBN) and 1,8-diazabicyclo (5,4,0) undec-7-ene (DBU) are commercially obtainable products, particularly DBU which is produced on an industrial scale.

C-7 methoxy derivatives of 7-aminocephalosporanic acids of Formula I have been prepared following the process of the Sankyo French patent application No. 75 35-009 with a view to forming the solutions with DBU and DBN; for example 7 beta-amino-7alpha-methoxy-3-(1(1H)tetrazol-5-yl)thiomethyl-3-cephem-4-carboxylic acid and 7beta-amino-7alpha-methoxycephalosporanic acid. Other 7-amino-3-heterocyclo-thiomethyl-3-cephem-4-carboxylic acids, described by DeMarinis et al. (J. Med. Chem. 19, 754, 1976) were prepared according to the method of Spanish Pat. No. 461.095. One example is 7-amino-3(4-methyl-1,2,4-triazol-3-yl-thiomethyl)-3-cephem-4-carboxylic acid.

For the practical purposes of the invention in the preparation of solutions, the corresponding 7-aminocephalosporanic acid of Formula I is suspended in the chosen solvent and, at a temperature of from 5° C. to room temperature there is added gradually the bicyclic amidine of Formula II, with good stirring, until solution is just obtained. The amount of DBN or DBU to be used is determined essentially by the stoichiometry of the reaction, generally at a rate of 1:1 and by the purity of the starting products.

To the thus prepared solution of a compound of Formula III there is added the acylating reactant, following the usual processes, the time, temperature and pH control being adjusted in each case to the peculiar characteristics of the reaction to obtain the desired cephalosporin.

Under the above conditions, the mixed anhydrides of the optically active enamine salts of p-hydroxyphenylglycine and phenylglycine have been effective with pivaloyl chloride and the corresponding chloride of tetrazolylacetic acid. Also the acids activated with dimethylformiminium chlorosulphite and, in general, the anhydrides and other usual reactants in this art.

Solvents appropriate for the purposes of the invention include dichloromethane, 1,2-dichloroethane, dimethylacetamide, acetonitrile, dimethylformamide, and mixtures with methylisobutylketone. Chloroform and nitromethane are also appropriate.

The pure 7-aminocephalosporanic acids of Formula I, treated with triethylamine, are completely insoluble in all of them, contrary to the results expressed by DeMarinis et al. (J. Med. Chem. 19, 754, 1976) and Gericke et al. (Arzneium.-Forsch., Drug, Res. 29 (I), 362; 1979).

An outstanding alternative in the new process consists of preparing the solution of 7-aminocephalosporanic acid of low purity. The impurities are precipitated out as solids or a pasty product by the gradual, controlled addition of methylisobutylketone or 1,2-dimethoxyethane. The clear solution is decanted and the white, high purity 7-aminocephalosporanic acid is precipitated out with acetic acid. Also, using 1,2-dimethoxyethane, the salt may be precipitated out and the impurities remain in the solution; in this case, the salt, preferably the DBU salt, is filtered.

An alternative technique to the process of said patent consists of the formation of the solutions at temperatures of $-20°$ to $0°$ C., by adjusting the amount of bicyclic amidine, DBN and DBU and the like and subsequently adding one equivalent of a triethylamine salt of a weak carboxylic acid such as pivalic acid, 2-ethylhexanoic acid, isononanoic acid and the like. The salts of such acids with tertiary bases, such as N-methylmorpholine, N-ethylpiperidine, n-tributylamine and the like may be used.

Clear, pale coloured solutions are prepared under these conditions and may be used for the subsequent acylation stage. A peculiarity of this class of solutions is that they give dark colours with impure 7-aminocephalosporanic acids, revealing the low quality of the product used.

The advantages offered by the process of the present invention are as follows:

1. A wider range of election of the organic solvents for the preparation of stable solutions.

2. The use of high purity 7-aminocephalosporanic acids.

3. Temperatures from $-20°$ to room temperature, in the solution preparation process.

4. The use of bicyclic amidines, cheaper compounds than the silylating reactants.

5. The absence of siloxanes in the reaction mixture which later make the recovery of the solvent difficult.

6. A simpler technology, since it is not necessary to retain the humidity and use an inert atmosphere in the chemical process.

7. The acylation reaction may be conducted within a wide range of temperatures.

8. Absence of restrictions in the use of activated carboxylic acids in any of the known forms thereof.

The results 2, 3, 4, 5, 6 and 8 do not occur with the usual methods of using silylating reactants, methanol and isopropanol being excluded in 1 as incompatible solvents, and those of case 1 are conceptually unstable to the humidity when referred to silyl esters.

A further important advantage is related to the isolation of the antibiotic. Countless examples describe mixtures of water and miscible organic solvent for preparing triethylamine solutions. The most usual are acetone and tetrahydrofurane. Together with the drawback of a partial hydrolysis of the acylation reactant, the cephalosporins formed are soluble. Therefore a common step to all cases is the distillation of the solvent at reduced pressure and treatments with successive extractions at different pH, representing a complicated technology and losses of yield, all of which is known to the experts in the matter and reflected in the patents.

The solutions of bicyclic amidine salts and a 7-aminocephalosporanic acid also reveal the presence of an amino group, at least as active as in the case of the esters and more active than in the N,O-bis-trimethylsilylated compounds in the solvent. The increased activity is determined by the relative acylation capacity and sensitivity to the temperature. Thus the conversion time may be adjusted in each case to obtain the best yields. A comparison of Examples 21 and 23 with 32 show the absence of alteration at very extended and short times. Example 31 proves that the reaction may be effectively performed at moderate temperatures, with better yields than those of Example 17 of German Pat. No. 2263861, where the reaction is held for 1 hour at $-35°$ and 3 hours at $-20°$ C. with a complex, time-consuming isolation method. German Pat. No. 27.58.000 describes the acylation reaction with a solution of 7-aminocephalosporanic acid and triethylamine, Example 6, gives a solution which may not be reproduced with the technically pure product. The following reaction with the 1-(alpha-sin-methoxymino-alpha(2-amino-tiazol-4-yl)acetoxy)-benzotriazole was conducted with low efficiency. On the other hand, better yields than disclosed in those Examples are obtained with the use of the solutions whose preparation is disclosed herein. In a similar way, better results are also obtained with these bicyclic amidine salts than those disclosed in Swiss Pat. No. 535.261 and in those described in the scientific literature (for example, Nannini et al., loc. cit.).

These solutions may be effectively used on an industrial scale for the acylation reactions with an active carboxylic acid, which it is wished to incorporate as a side chain in C-7, to prepare an acylamine derivative of 7-aminocephalosporanic acid. Thus, depending on the acid to be incorporated, active forms include the acid anhydride, the mixed anhydride of weak or strong acids, such as a monoester of carbonic acid, alkyl or arylsulphonic and hindered acids such as trimethylacetic acid, trichloroacetic acid and diphenylacetic acid. Additionally, an azide of an acid, an active ester or active thioester (example, p-nitrophenol, 2,4-dinitrophenol, thiophenol, N-hydroxysuccinimide, N-hydroxyphthalimide, N-hydroxybenzotiazole); the acid itself may be incorporated with the aid of dimethylforminium chlorosulphite, N,N'-carbonylimidazole or N,N'-carbonylditriazole and carbodiimides (particularly N,N'-dicyclohexylcarbodiimide, N,N'-diisopropylcarbodiimide or N-cyclohexyl-N'-(2-morpholinethyl)carbodiimide; Sheehan and Hess, J. Amer. Chem. Soc., 77, 1067 (1955)) or an alkylamine reactant (Buijili and Viehe, Agnew, Chem. Inter. Edi., 3,582 (1964) or ketenimines (Stevens and Munk, J. Amer. Chem. Soc. 80, 4065 (1958) or a reactive salt of isoxazolonium (Woodward, Olofson and Mayer, J. Amer. Chem. Soc., 83.1010 (1961)). The active amides such as the azolides or in which the nitrogen atom is a member of a quasiaromatic ring of five members containing at least two atoms of nitrogen, for example, imidazoles, pyrazoles, triazoles, benzimidazoles, benzotriazoles and the substituted derivatives thereof as also condensed heterocycles may be used. Active forms of carboxylic acids also include mixed anhydrides of phosphorous compounds. All of them are widely known and described in the scientific and technical literature.

In the case of activated acids which, in the acylation process release an acid equivalent, the effect of the acid is eliminated with the use of the solutions described in the present invention or by incorporating a further bicyclic amidine equivalent into the medium.

The mixture resulting from the acylation reaction with these solutions requires simple treatments for the isolation of the corresponding cephalosporins and these are reflected with some examples described. On the other hand the isolation methods published (e.g. Nannini et al., loc. cit., page 352) and those described in British Pat. No. 1,319,173 are very time-consuming and difficult in industrial practice to attain the cephalosporins 3-substituted with thiomethylheterocycles.

EXAMPLE 1

7-amino-3(5-methyl-1,3,4-thiadiazol-2-yl-thiomethyl)-3-cephem-4-carboxylic acid

To a suspension of 34.44 g of the compound of the title in 600 ml of dichloromethane, under stirring at room temperature (20° C.), there was added gradually DBU until complete solution was obtained, about 16 ml of bicyclic amidine being required. The solution was then cooled to 5° C. for subsequent use.

EXAMPLE 2

7-amino-3-desacetoxycephalosporanic acid

To a suspension of 21.42 g of the compound of the title in a mixture of 200 ml of methylisobutylketone and 200 ml of dimethylformamide, under stirring at 20° C., there was added 16 ml of DBU, a solution being formed immediately. This was cooled to 0° C., ready for use.

EXAMPLE 3

7-amino-3-desacetoxycephalosporanic acid

To a suspension of 21.42 g of the compound of the title in a mixture of solvents as per Example 2, there was added a sufficient amount, between 100 and 200 ml, of methylisobutylketone, at a temperature of 0°–5° C. to cause the separation of impurities. The liquids were decanted, the pH was adjusted with acetic acid (neutralisation of the DBU) and the white, crystalline 7-ADCA precipitate, after filtration, washing with acetone and drying, was treated as in Example 2.

EXAMPLE 4

7-amino-3-(5-methyl-1,3,4-thiadiazol-2-yl-thiomethyl)-3-cephem-4-carboxylic acid Following Example 1 and replacing the DBU with 12 ml of DBN, a solution was obtained.

EXAMPLE 5

7 beta-amino-7 alpha-methoxy-3(1H-tetrazol-5-yl-thiomethyl)-3-cephem-4-carboxylic acid To a suspension of 17.18 g of the compound of the title in 300 ml of dichloromethane, under stirring at room temperature, there was gradually added 8 ml of DBU until complete solution was obtained. The solution was subsequently cooled to 5° C. for later use.

EXAMPLE 6

7-amino-3-(4-methyl-1,2,4-(triazol-3-yl-thiomethyl)-3-cephem-4-carboxylic acid

To a suspension of 16.36 g of the compound of the title in 200 ml of dimethylacetamide, under stirring at 10° C., there was added gradually about 6 ml of DBN, until complete solution was obtained; the solution was then cooled to −5° C. for later use.

EXAMPLE 7

7-aminocephalosporanic acid

To a suspension of 27.22 g of 7-ACA in 200 ml of acetonitrile, under stirring at 20° C., there was added about 12 ml of DBN, a solution being formed instantaneously. The solution was filtered as required and thereafter cooled to 0°–5° C.

EXAMPLE 8

7-amino-3-desacetoxycephalosporanic acid

To a suspension of 21.42 g of the compound of the title in 200 ml of 1,2-dichloroethane, under stirring at 20° C., there was added gradually about 16 ml of DBU, total solution being obtained in 10 minutes.

EXAMPLE 9

7-aminocephalosporanic acid

Following Example 7 and replacing the DBN with 16 ml of DBU, a solution was formed almost instantaneously.

EXAMPLE 10

7-amino-3-(5-methyl-1,3,4-thiadiazol-2-yl-thiomethyl)-3-cephem-4-carboxylic acid To a mixture of 34.44 g of the compound of the titles in 200 ml of dimethylacetamide, under stirring at 20° C., there was added gradually about 16 ml of DBU, a solution being formed.

EXAMPLE 11

7 beta-amino-7 alpha-methoxy-3(acetoxymethyl)-3-cephem-4-carboxylic acid

To a suspension of 15 g of the compound of the title in 200 ml of dichloroethane, under stirring at room temperature, there was added 7.5 ml of DBU, followed by final adjustment until a complete solution was obtained. The solution was then cooled to 5° C. for later use.

EXAMPLE 12

7-aminodesacetoxycephalosporanic acid

To a suspension of 18.9 g of the compound of the title in 150 ml of dichloromethane, there was added 14.8 ml of DBU, under stirring at 10° C. A solution was formed at 10° C. and was subsequently cooled to −35° C.

EXAMPLE 13

7-aminocephalosporanic acid

To a mixture of 27.22 g of the compound of the title in 200 ml of methylisobutylketone and 200 ml of dimethylformamide, under vigorous stirring at 22° C., there was gradually added 12 ml of DBN. The solution was filtered after 10 minutes as required and the liquid was cooled to −5° C.

EXAMPLE 14

7-amino-3-(5-methyl-1,3,4-thiadiazol-2-yl-thiomethyl)-3-cephem-4-carboxylic acid 34.44 g of the compound of the title were added to 250 ml of 1,2-dichloroethane and while the mixture was being stirred at room temperature, 16 ml of DBU were added gradually until complete solution was obtained. The solution was then cooled to 5° C. for later use.

EXAMPLE 15

7-amino-3-(5-methyl-1,3,4-thiadiazol-2-yl-thiomethyl)-3-cephem-4-carboxylic acid 34.44 g of the compound of the title were added to 250 ml of 1,2-dichloroethane and while the mixture was being stirred at room temperature, 12 ml of DBN were added gradually, the amount being adjusted as required to obtain total solution. The solution was then cooled to 5° C. for later use.

EXAMPLE 16

Following Example 14 and replacing the 1,2-dichloroethane with dimethylacetamide, a solution is formed in a short time.

EXAMPLE 17

7-aminodesacetoxycephalosporanic acid

To a suspension of 21.42 g of the compound of the title in 200 ml of chloroform, under stirring at room temperature, there was added gradually 16 ml of DBU, the amount being adjusted as required. A solution was formed almost immediately and it was cooled to 5° C. for use.

EXAMPLE 18

7-aminodesacetoxycephalosporanic acid

To a suspension of 21.42 g of the compound of the title in 200 ml of nitromethane, under stirring at room temperature, there was added gradually 16 ml of DBU, the amount of the latter being adjusted, until complete solution which occured in 5 minutes. The solution was cooled to the desired temperature for later use.

EXAMPLE 19

7-beta-amino-7-alpha-methoxy-3-(acetoxymethyl)-3-cephem-4-carboxylic acid

Following Example 14 and replacing the cephalosporanic acid with 15 g of the compound of the title, a solution was formed in a short time.

EXAMPLE 20

7-amino-3-(4-methyl-1,2,4-triazol-3-yl-thiomethyl)-3-cephem-4-carboxylic acid

Following Example 14 and replacing the cephalosporanic acid with 17.18 g of the compound of the title, a solution was formed in a short time.

EXAMPLE 21

7-(1(1H)-tetrazolylacetamido)-3-[2-(5-methyl-1,3,4-thiadiazolyl)thiomethyl]3-cephem-4-carboxylic acid To a solution of 34.44 g of the compound prepared according to Example 1 and cooled to 5° C., there was added 12 ml of triethylamine and thereafter it was poured over a period of 15 minutes over a further solution of the mixed anhydride of tetrazolylacetic acid prepared with 15.3 g of acid, 17 ml of triethylamine in 150 ml of dichloromethane and 14.5 ml of pivaloyl chloride at a temperature of −5° C. to 0° C. (30 minutes stirring). The reaction mixture was stirred for 60 minutes at −5° C. Thereafter, it was extracted with portions of water and the aqueous extracts were combined, 1000 ml, were adjusted to pH 1.50 by addition of hydrochloric acid, while being cooled by ice water bath (5° C.). N-hexane was added, stirring was continued for a further 15 minutes and the precipitate was filtered, washed and dried to give 40.5 g of the compound of the title. This was suspended in ethyl acetate and heated to reflux with stirring for 30 minutes. It was filtered while hot, to give the acid with a m.p. 189°-190° C. (d) and $[alpha]_D^{20} = -50°$ (C=1%, dimethylsulphoxide).

EXAMPLE 22

7-amino-3-(3-methylisoxazol-5-yl)-carbonylthiomethyl-3-cephem-4-carboxylic acid

To a suspension of 3.79 g of the compound of the title in 50 ml of dichloromethane with 1 ml of methanol, cooled to −10° C., there was added 1.50 ml of DBH. With stirring the mixture soon formed a solution which was adjusted with a few drops of DBU according to its purity. Thereafter, there was added one equivalent of triethylamine pivalate, no precipitate being formed.

EXAMPLE 23

7-amino-3-(1-methyl-1,2,3,4-tetrazol-5-yl-thiomethyl)-3-cephem-4-carboxylic acid To a suspension of 3.28 g of the compound of the title in 50 ml of dichloromethane, cooled to −10° C., there was added 1.60 ml of DBU, a solution being formed immediately. To this there was added one equivalent of triethylamine 2-ethylhexanoate, no precipitate being formed.

EXAMPLE 24

Following the previous Example, and replacing the dichloromethane with 30 ml of methanol, a solution was formed. No precipitate was formed with the addition of triethylamine pivalate.

EXAMPLE 25

Following Example 23 and replacing the dichloromethane with 30 ml of acetonitrile and the DBU with 1.20 ml of DBN, a solution was formed, from which no precipitate was obtained with the addition of triethylamine pivalate.

EXAMPLE 26

Following Example 23 and replacing the dichloromethane with 40 ml of 1,2-dichloroethane and the DBU with 1.2 ml of DBN, a solution was formed. No precipitate was formed with the addition of triethylamine 2-ethylhexanoate or triethylamine pivalate.

EXAMPLE 27

7-amino-3-(2-amino-1,3,4-thiadiazol-5-yl-thiomethyl)-3-cephem-4-carboxylic acid

To a suspension of 3.45 g of the compound of the title in 20 ml of methanol at −10° C., under stirring, there was added 1.55 ml of DBU. A solution was formed after 10 minutes and it was adjusted with a few drops of DBU as required. No precipitate was produced with the addition of triethylamine pivalate.

EXAMPLE 28

Following Example 27 and replacing the methanol with 40 ml of 1,2-dichloroethane and 8 ml of methanol a solution was formed.

EXAMPLE 29

Following Example 27 and replacing the methanol with a mixture of 40 ml of dichloromethane and 8 ml of methanol, a solution was formed. No precipitate was formed with the addition of triethylamine pivalate.

EXAMPLE 30

7-amino-3-azidomethyl-3-cephem-4-carboxylic acid

To a suspension of 2.51 g of the compound of the title in 20 ml of dichloromethane at −10° C., there was added 1.20 ml of DBN, adjusted with a further amount of base according to its purity. A solution was formed in a short time and no precipitate was formed with the addition of triethylamine 2-ethylhexanoate.

EXAMPLE 31

Following Example 30 and replacing the dichloromethane with 1,2-dichloroethane, a solution was formed.

EXAMPLE 32

Following Example 30 and replacing the dichloromethane with acetonitrile, a solution was formed.

EXAMPLE 33

Following Example 30 and replacing the dichloromethane with dimethylacetamide, a solution was formed.

EXAMPLE 34

Following Example 30 and replacing the dichloromethane with dimethylformamide and the DBN by the equivalent amount of DBU a solution was formed.

EXAMPLE 35

Following Example 30 and replacing the dichloromethane with nitromethane and the DBN with the equivalent amount of DBU, a solution was formed.

EXAMPLE 36

Following Example 30 and replacing the dichloromethane with chloroform, a solution was formed.

EXAMPLE 37

7-amino-3-(1-phenyl-tetrazol-2-yl-thiomethyl)-3-cephem-4-carboxylic acid

To a suspension of 3.90 g of the compound of the title in 20 ml of dichloromethane at −10° C., there was added 1.55 ml of DBU, the mixture being adjusted according to the purity of the base. An instantaneous solution was formed, but the addition of triethylamine 2-ethylhexanoate did not cause any precipitate.

EXAMPLE 38

Following Example 37 and replacing the dichloromethane by 40 ml of acetonitrile and the DBU with 1.20 ml of DBN, a solution was obtained which gave no precipitation on the addition of triethylamine pivalate.

EXAMPLE 39

7-amino-3-azidomethyl-3-cephem-4-carboxylic acid

To a suspension of 2.54 g of the compound of the title in 20 ml of isopropanol there was added 1.20 ml of DBN, with adjustment according to the purity of the base. A solution was formed in a short time but which gave no precipitation on the addition of triethylamine pivalate.

EXAMPLE 40

7-amino-3-acetoxymethyl-3-cephem-4-carboxylic acid

To a suspension of 13.6 g of the compound of the title in 100 ml of isopropanol there was added 6.0 ml of DBN with adjustment according to the purity of the base. A solution was formed after about 15 minutes stirring, from which no precipitate was formed on addition of triethylamine pivalate.

EXAMPLE 41

7-amino-3-(5-methyl-1,3,4-thiadiazol-2-yl-thiomethyl)-3-4-carboxylic acid

To a suspension of 17.2 g of the compound of the title in 100 ml of methanol at −20° C., there was added 12.0 ml of DBU, a solution being formed instantaneously.

EXAMPLE 42

7-amino-3-(1,2,3-triazol-5-yl-thiomethyl)-3-cephem-4-carboxylic acid

To a suspension of 3.13 g of the compound of the title in 30 ml of dichloromethane at −15° C., there was added 1.55 ml of DBU and a solution was formed. One equivalent of triethylamine pivalate was added but there was no precipitate.

EXAMPLE 43

7-amino-3(1,3,4-thiadiazol-2-yl-thiomethyl)-3-cephem-4-carboxylic acid

To a suspension of 3.30 g of the compound of the title in 30 ml of 1,2-dichloroethane, there was added 1.20 ml of DBN, with adjustment according to the purity of the base. A solution was formed after stirring for a short time at −5° C., but no precipitate was formed therein on the addition of one equivalent of the triethylamine salt of isononanoic acid.

EXAMPLE 44

7-amino-3-acetyl-thiomethyl-3-cephem-4-carboxylic acid

To a suspension of 288 g of the compound of the title in 30 ml of dichloroethane at −10° C., there was added 1.55 ml of DBU with adjustment according to the purity of the base. A solution was formed after stirring for a short time but no precipitate was formed on addition of triethylamine pivalate.

EXAMPLE 45

Following Example 44 and replacing the compound of the title with the corresponding 3-phenylthiomethyl derivative, a solution is formed which, on addition of triethylamine pivalate, does not form a precipitate.

EXAMPLE 46

7beta-amino-7alpha-methoxy-3-acetoxymethyl-3-cephem-4-carboxylic acid

To a suspension of 3.02 g of the compound of the title in 30 ml of chloroform at −10° C. there was added 1.55 ml of DBU with adjustment according to the purity of the base. A solution was formed after a short time, but no precipitate was formed on addition of triethylamine pivalate.

EXAMPLE 47

7-amino-3-(5-methyl-1,3,4-thiadiazol-2-yl)-3-cephem-4-carboxylic acid

To a solution of 2.98 g of the compound of the title in 35 ml of dichloromethane at −10° C., there was added 1.20 ml of DBN with adjustment according to the purity of the base. A solution was formed after a short time, but no precipitate was formed by addition of one equivalent of N-ethylpiperadine 2-ethylhexanoate.

EXAMPLE 48

7-amino-3-(1(H)-5-methyl-1,3,4-triazole-2-yl)-3-cephem-4-carboxylic acid

To a suspension of 2.81 g of the compound of the title in 30 ml of dichloromethane at −5° C., there was added 1.20 ml of DBN with adjustment according to the purity of the base. A solution was formed in a short time but there was no precipitate formed on addition of N-methylmorpholine isononanoate.

EXAMPLE 49

7-amino-3-(phenyl-thiomethyl)-3-cephem-4-carboxylic acid

To a suspension of 3.23 g of the compound of the title in 25 ml of dichloroethane at −10° C., there was added one equivalent of bicyclic amidine, DBN, DBU or other similar compound. The amount of base was adjusted according to its purity and a solution of the corresponding salt was formed after stirring for a short time.

EXAMPLE 50

Following Example 49 and replacing the dichloromethane with chloroform, a solution of the corresponding salt was formed.

EXAMPLE 51

7-amino-3-(gamma-pyridyl-thiomethyl)-3-cephem-4-carboxylic acid

To a suspension of 3.24 g of the compound of the title in 30 ml of acetonitrile at −10° C., there was added one equivalent of bicyclic amidine, DBN, DBU or other similar product. The amount of base was adjusted according to its purity and a solution of the corresponding salt was formed.

EXAMPLE 52

7-(1(1H)-tetrazolylacetamido)-3-[2-(5-methyl-1,3,4-thiadiazolyl)thiomethyl]-3-cephem-4-carboxylic acid To a suspension of 10.75 g of technically pure 7-amino-3-(5-methyl-1,3,4-thiadiazol-2-yl-thiomethyl)-3-cephem-4-carboxylic acid, in 150 ml of dichloromethane at a temperature of −10° C., there was added 6.25 ml of 1,8-diazobicyclico-(5,4,0) undec-7-ene (DBU) and a solution was formed instantaneously. To this there was added triethylamine pivalate prepared with 1.5 g of pivalic acid and 4.0 ml of triethylamine. Thereafter, 9,5 g of tetrazolylacetic anhydride was added at one time. The solution was stirred for 90 minutes at 0°–5° C. The reaction mixture was raised to 15° C. and 325 ml of water were added with a few drops of a sodium dioctylsulphosuccinate solution. The mixture, at pH 3.5 (at 20° C.) develops in one minute to pH 3.8 at 20° C., and drops after about 15 minutes to pH 3.63 (22° C.). The slight brown precipitate (0.50 g) was isolated. The water phase was decanted off and decoloured with 2.5 g of active carbon for 15 minutes, the pH being 4.48. The mixture was filtered (a 0.025 g portion of the product was isolated from the carbon with an aqueous triethylamine solution). 250 ml of methylisobutylketone were added to the aqueous liquors and the pH was gradually raised to 3.0 (23° C.), 1.0 g of a yellowy product being precipitated. The liquors decanted colourless and with 1 N hydrochloric acid.

What we claim is:

1. A process for the preparation of solutions of 7-aminocephalosporanic acids which comprises forming a suspension, in an organic non-aqueous solvent, of a compound of the formula

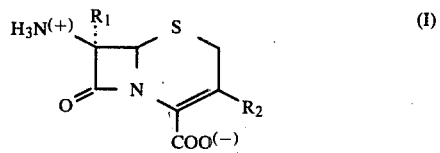

wherein $R_1$ is a member of the group consisting of hydrogen, methyl, methoxy, ethoxy, or isopropoxy and $R_2$ is a member of the group consisting of methyl, methoxy, azido, chloro, carbamoylmethyl, acetoxy, thiomethyl, phenylmethyl, alkylthiocarbonyl, arylthiocarbonyl, methylthiocarbonyl heterocyclic heterocyclic derivative having a five or six member ring with at least one atom of oxygen, sulphur or nitrogen, methylthioheterocycles of thiazole, thiadiazole, triazole, tetrazole, pyridine, pirimidine or of a heterocycle condensed to an aromatic ring, such as thiadiazole, oxadiazole or triazole or a thiadiazolyl, oxadiazolyl or triazolyl radical, is associated by a salt-forming reaction with a bicyclic amidine having the formula:

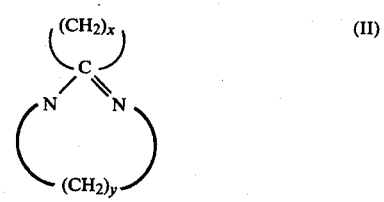

where X is from 3 to 5 carbon atoms and Y from 2 to 4 carbon atoms, to obtain a solution of the corresponding salt of 7-aminocephalosporanic acid having the formula:

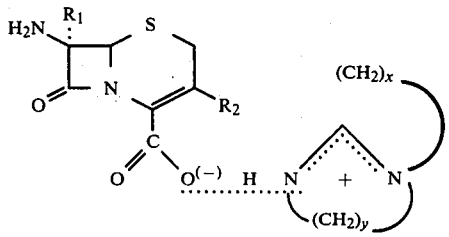
(III)

2. The process of claim 1, in which the bicyclic amidine is 1,5-diazobicyclo(4,3,0)non-5-ene having the formula:

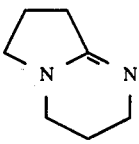

3. The process of claim 1, in which the bicyclic amidine is 1,8-diazabicyclo(5,4,0)undec-7-ene having the formula:

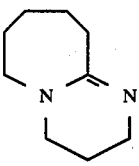

4. The process of claim 1, in which the organic non-aqueous solvent is selected from among the group consisting of dichloromethane, dimethylacetamide, 1,2-dichloroethane, chloroform, nitromethane, dimethylformamide, acetonitrile, methylisobutylketone, methanol, isopropanol or mixtures thereof.

5. The process of claim 1, characterised in that to a solution in an organic non-aqueous solvent resulting from the reaction of a selected compound of formula I with a selected compound of formula II, there is added a precipitating agent selected from the group comprising methylisobutylketone, 1,2-methoxyethane and ethyl acetate, to obtain the corresponding salt of the bicyclic amidine of formula II in pure form and to obtain a salt of formula III.

6. The process of claim 1, characterised in that a suspension of a 7-aminocephalosporanic acid in an organic non-aqueous solvent selected from among the group comprising methanol, isopropanol, dichloromethane, 1,2-dichloroethane, chloroform, acetonitrile, dimethylformamide, dimethylacetamide, nitromethane and the like, or mixtures thereof, at $-20°$ C., is reacted with a bicyclic amidine selected from among the group comprising 1,5-diazabicyclo(4,3,0) non-5-ene, 1,8-diazabicyclo(5,4,0)undec-7-ene and the like, to obtain a solution of the corresponding salt of 7-aminocephalosporanic acid, there being added thereafter a tertiary amine salt, such as triethylamine and a carboxylic acid selected from among the group comprising trimethylacetic, 2-ethylhexanoic, isononanoic acid and the like, to obtain a solution useful for subsequent reaction with the active form of a carboxylic acid.

7. A process of claim 1, in which the alkylthiocarbonyl is selected from the group consisting of methylthiocarbonyl, ethylthiocarbonyl, propylthiocarbonyl and butylthiocarbonyl.

* * * * *